(12) United States Patent
Aughton et al.

(10) Patent No.: US 8,915,131 B2
(45) Date of Patent: Dec. 23, 2014

(54) METHOD OF DETERMINING SURFACE LEVEL, AND A SOIL MOISTURE SENSOR

(75) Inventors: David John Aughton, Hawthorn East (AU); Damien Vernon Pearson, Kew East (AU)

(73) Assignee: Rubicon Research Pty Ltd., Hawthorn, Victoria (AU)

( * ) Notice: Subject to any disclaimer, the term of this patent is extended or adjusted under 35 U.S.C. 154(b) by 382 days.

(21) Appl. No.: 13/409,013

(22) Filed: Feb. 29, 2012

(65) Prior Publication Data

US 2012/0152012 A1 Jun. 21, 2012

Related U.S. Application Data

(63) Continuation of application No. PCT/AU2010/001125, filed on Sep. 1, 2010.

(30) Foreign Application Priority Data

Sep. 3, 2009 (AU) .............................. 2009904225

(51) Int. Cl.
*E21B 47/00* (2012.01)
*A01G 25/16* (2006.01)
*G01F 23/00* (2006.01)
*G01N 33/24* (2006.01)

(52) U.S. Cl.
CPC .......... *A01G 25/167* (2013.01); *G01F 23/0061* (2013.01); *G01N 33/246* (2013.01)
USPC ..................................................... 73/152.01

(58) Field of Classification Search
CPC ...... G01N 33/246; E21B 47/042; E02B 13/00

USPC ....................................................... 73/152.01
See application file for complete search history.

(56) References Cited

U.S. PATENT DOCUMENTS 688,607 A 12/1901 Dixon
3,129,413 A * 4/1964 Watson ......................... 340/521
(Continued)

FOREIGN PATENT DOCUMENTS

| CN | 2367083 | 3/2000 |
| SU | 518707 | 7/1976 |
| SU | 1264056 | 10/1986 |

OTHER PUBLICATIONS

Australian Patent Application No. 2010291862, Patent Examination Report No. 1 mailed Dec. 5, 2013.
(Continued)

*Primary Examiner* — John Fitzgerald
(74) *Attorney, Agent, or Firm* — Sheppard, Mullin, Richter & Hampton LLP (57) ABSTRACT

A method of determining the surface level of an area subject to flood, furrow or surface irrigation. The method includes the steps of providing at least one measuring cup positioned below the surface level but within the area and providing a water level sensor within or integrated with the at least one measuring cup. The levels provided by the water level sensor are used to calculate the surface level by determining the inflection point between the rapid increase of the monitored levels when the front of irrigation water passes the water level sensor. A further aspect of the disclosure is the provision of a soil moisture sensor, said sensor comprising an auger adapted to be inserted into the ground with minimum soil disturbance, said auger having means for measuring soil moisture.

8 Claims, 5 Drawing Sheets

(56) References Cited

U.S. PATENT DOCUMENTS

| | | | | |
|---|---|---|---|---|
| 3,952,522 | A | * | 4/1976 | Shettel ................... 405/37 |
| 3,960,107 | A | | 6/1976 | McCloskey |
| 4,431,338 | A | | 2/1984 | Hornabrook |
| 4,464,079 | A | * | 8/1984 | Chance .................. 405/37 |
| 4,522,534 | A | * | 6/1985 | Wakamori et al. ........ 405/37 |
| 4,929,885 | A | * | 5/1990 | Dishman ................ 324/664 |
| 5,224,837 | A | * | 7/1993 | Lamphere et al. ........ 417/63 |
| 5,269,184 | A | | 12/1993 | Nishida |
| 5,341,831 | A | | 8/1994 | Zur |
| 5,613,803 | A | * | 3/1997 | Parrish .................. 405/92 |
| 5,667,336 | A | | 9/1997 | Zur |
| 6,441,622 | B1 | * | 8/2002 | Wrzesinski et al. ...... 324/643 |
| 6,532,803 | B2 | * | 3/2003 | Hutchinson et al. ....... 73/73 |
| 6,742,405 | B2 | * | 6/2004 | Hubbell et al. ........ 73/863.23 |
| 6,956,381 | B2 | * | 10/2005 | Dahan ................... 324/643 |
| 7,152,001 | B2 | * | 12/2006 | Aughton et al. ............ 702/2 |
| 7,176,697 | B1 | * | 2/2007 | Dahan ................... 324/643 |
| 2003/0024155 | A1 | | 2/2003 | Kuroda et al. |

OTHER PUBLICATIONS

Chinese Patent Application No. 201080039340.5, Second Office Action mailed Aug. 9, 2013.

Wood, M. et al., "Real-Time Monitoring and Control of On-Farm Surface Irrigation Systems," National Program for Irrigation Research and Development, Jul. 1998. Retrieved from the Internet on Jun. 29, 2012 from http://npsi.gov.au/files/products/national-program-sustainable-irrigation/er980345/er980345.pdf.

Humpherys, A. et al., "Water Sensor Feedback Control Systems for Surface Irrigation," Applied Engineering in Agriculture, vol. 11, No. 1, pp. 61-65, Jan. 1995. Retrieved from the internet on Jun. 29, 2012 from http://eprints.nwisrl.ars.usda.gov/634/1/856.pdf.

International Application No. PCT/AU2010/001125, International Search Report and Writtetn Opinion mailed Nov. 26, 2010.

Chinese Patent Application No. 201080039340.5, Office Action mailed Jan. 29, 2013.

European Patent Application No. 10813158.2, Search Report mailed Apr. 22, 2014.

* cited by examiner

METHOD OF DETERMINING SURFACE LEVEL, AND A SOIL MOISTURE SENSOR

CLAIM OF PRIORITY

This application is a continuation of and incorporates by reference International Application No. PCT/AU2010/001125, filed Sep. 1, 2010 and published as WO 2011/026177 A1 on Mar. 10, 2011, entitled "A Method of Determining Surface Level, and a Soil Moisture Sensor," which claims priority to Australian Patent Application Ser. No. 2009904225, filed Sep. 3, 2009.

FIELD OF THE INVENTION

The present invention relates to a method of determining the surface level at a location of an area subject to flood, furrow or surface irrigation and relates particularly, though not exclusively, to determining the depth of water and the volume of water above the surface level. This method also defines when the surface irrigation water front arrives at the location.

BACKGROUND OF THE INVENTION

Flood, furrow or surface irrigation is a method of passing a volume of water over a confined surface in order to achieve a desired soil infiltration. Modern laser-grading techniques have allowed large areas (or bays) to be defined and accurately graded so that improved efficiencies can be achieved. In addition, high flows of water onto bays are resulting in improved water application efficiencies on many soil types. Most bays are rectangular in shape and graded to a uniform slope.

The challenge is to apply the correct amount of water to an irrigated crop using flood or surface irrigation such that:
1. The depth of infiltration is consistent with the required depth of infiltration of the crop throughout the entire bay.
2. There is no over-watering such that no excess water runs off the end of the bay, and no under-watering such that water does not reach the end of the bay—the precise time to stop the flow onto the bay.

The difficulties in this task are:
a. The infiltration rate of the soil is unknown, and so although the volume of water applied is known (by multiplying the time of application by the measured flow rate), the infiltrated volume is unknown and so the remaining volume of water above the surface must be measured.
  Although the infiltration rate is likely to be consistent across the bay, it can vary from irrigation to irrigation.
b. To determine the volume of water above the surface, the depth of water above the surface must be measured and multiplied by the area of coverage. The difficulty in measuring depth is defining the surface level, or the datum above which the depth is measured. The depth of flow can vary from irrigation to irrigation due to factors such as crop density and resistance it makes to the flow or the existing soil moisture.
c. Traditional measurement of the ground level is not a simple or reliable process, as it requires a detailed survey to determine the mean ground level. It is difficult to achieve the required accuracy due to the localized unevenness of the soil and to determine the point at which to record the surveyed surface level measurement. To reduce this error, many measurements need to be taken from which to derive the mean ground level.

Objects of the Invention

Accordingly it is an object of the present invention to provide a method of determining the surface level of an area subject to flood or surface irrigation which overcomes these problems and allows an accurate measurement of the surface level.

A further object of the invention is to allow calculation of the volume of water needed for the desired irrigation.

SUMMARY OF THE INVENTION

In a first aspect of the invention there is provided a method of determining the surface level of an area subject to flood, furrow or surface irrigation, said method including the steps of providing at least one measuring cup positioned below the surface level but within said area, providing a water level sensor within or integrated with said at least one measuring cup, monitoring the levels provided by said water level sensor and calculating said surface level by determining the change point between the rapid increase of said monitored levels when the front of said irrigation water passes said water level sensor.

In a still further form of the invention there is provided a soil moisture device including an auger adapted to be inserted into the ground with minimum soil disturbance and means on said auger to measure soil moisture.

In a yet further form of the invention there is provided a method of determining the volume of water of an area subject to flood, furrow or surface irrigation, said method including the steps of providing at least one measuring cup positioned below the surface level of the ground but within said area, providing a water level sensor within or integrated with said at least one measuring cup, monitoring the levels provided by said water level sensor and calculating said surface level by determining the change point between the rapid increase of said monitored levels when the front of said irrigation water passes said water level sensor and calculating the volume by using the difference between said calculated surface level of the ground and the detected water levels from said water level sensor after the passing of said irrigation water front.

BRIEF DESCRIPTION OF THE DRAWINGS

The accompanying drawings, which are incorporated in and constitute a part of this specification, illustrate an implementation of the invention and, together with the description, serve to explain the advantages and principles of the invention. In the drawings.

DESCRIPTION OF THE PREFERRED EMBODIMENTS

The following detailed description of the invention refers to the accompanying drawings. Although the description includes exemplary embodiments, other embodiments are possible, and changes may be made to the embodiments described without departing from the spirit and scope of the invention.

Wherever possible, the same reference numbers will be used throughout the drawings and the following description to refer to the same and like parts. For the purposes of the specification the word "comprising" means "including but not limited to", and the word "comprises" has a corresponding meaning. Also a reference within the specification to document or to prior use is not to be taken as an admission that the disclosure therein constitutes common general knowledge in Australia.

Figure 1:
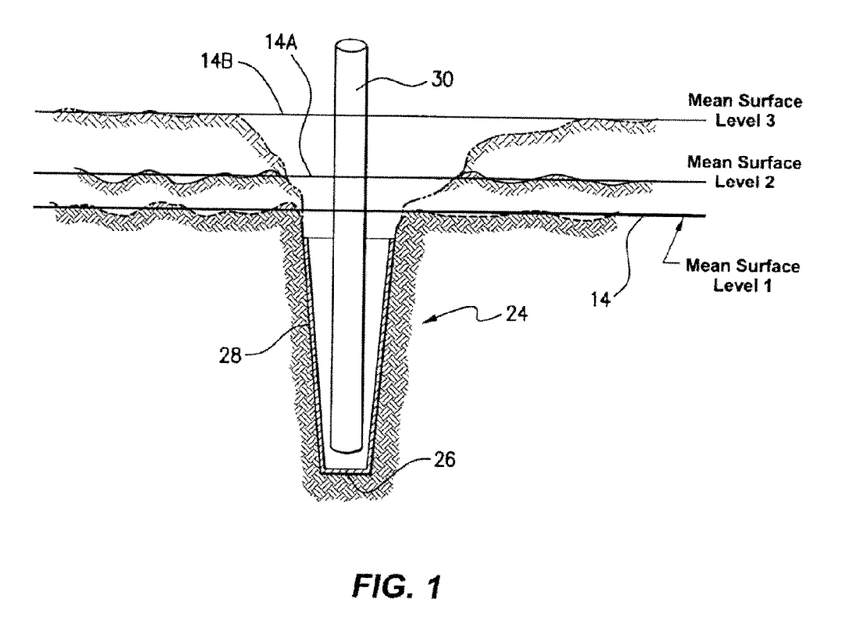
FIG. 1 is a cross-sectional view of an example of a measuring cup and level sensor used in a preferred embodiment of the invention.
Figure 2:
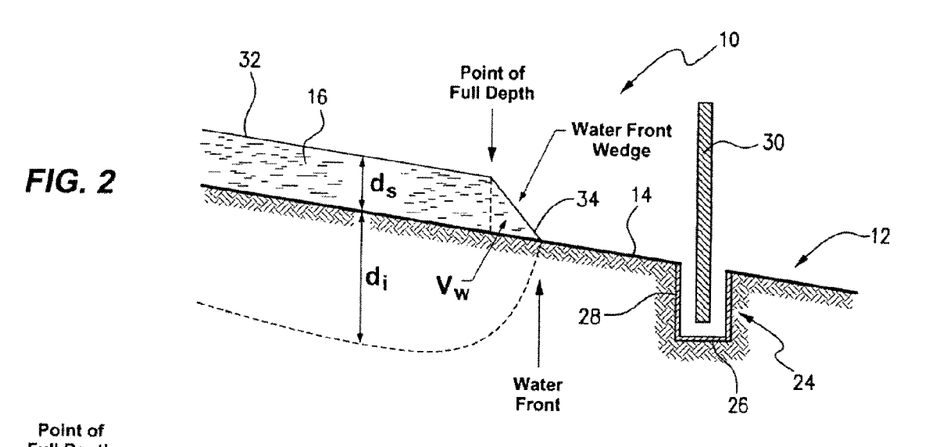
FIG. 2 is a similar view to that of FIG. 1 showing the water flow of an area subject to flood irrigation with the measuring cup and level sensor in position.

In FIGS. 1 to 4 of the drawings there is shown an irrigation system 10 which incorporates the features of the invention. The irrigation system 10 has a bay 12 which has the ground 14 graded to provide a slope. Water 16 can flow through a gate or gates 18 from an open channel 20. Water flows along the ground slope 14 and any excess water will be caught by open channel 22 at the end of bay 12. The theory is to provide enough water to provide a consistent infiltration into the ground for the crop being grown but not to have insufficient or excess water draining into open channel 22. The amount of water entering gate or gates 18 can be accurately measured for ensuring that the water allotment is not exceeded. However it is difficult to determine whether under-or over-watering occurs. The invention provides a measuring cup 24 which is set into the ground 14 and is below ground level. Measuring cup 24 can be any shape, for example cylindrical, and has a base 26 and sidewalls 28. In FIG. 1 the sidewalls 28 are tapered to form a frusto-conical shape. Located within measuring cup 24 is a water level sensor 30 which can constantly detect the level of water 16 passing at that point. The water levels are constantly monitored by a computer controlled system (not shown) which can supervise operation of gate or gates 18.

Figure 3:
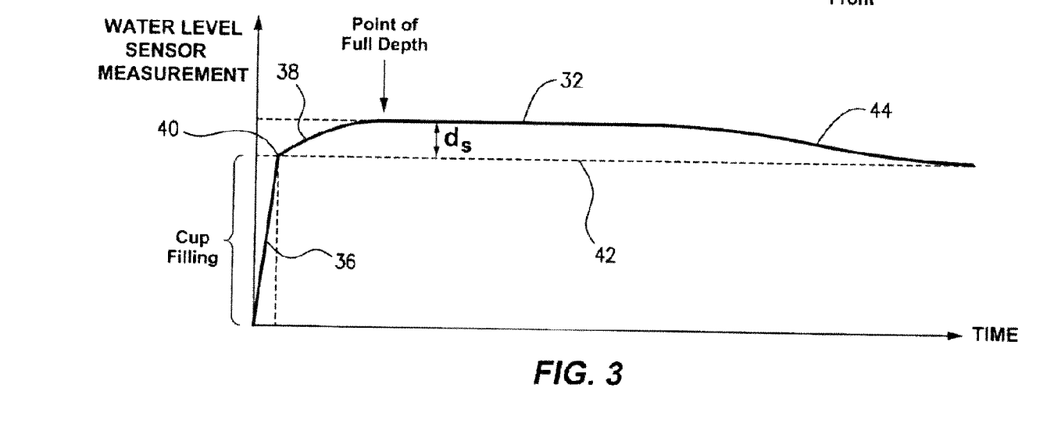
FIG. 3 is a graphical representation of the water level measurement of the level sensor in FIG. 2 against time.

The invention provides a method to determine the surface level 42 by measuring the rise of water in measuring cup 24. There will be a rapid rise of the water level in measuring cup 24 which is filled when water front 34 reaches measuring cup 24. Once measuring cup 24 fills, the localized effect disappears and the movement of the passing water front 34 controls the rise in water level. The point of change 40 between the rapid rise 36 of the filling of measuring cup 24 and the more gradual rise 38 of the passing of the water front 34 is the point of the surface level 42 of ground 14 at the position of measuring cup 24. FIG. 1 also shows that the measuring cup 24 can vary in depth in the ground. FIG. 1 shows a typical ground level 14 but the ground level could be higher as shown at 14A and 14B. In the levels at 14A and 14B there will be a greater filling time before the water flows past the water level sensor 30 as the water front passes.

Similarly the passing of the water front (the tailwater 44) is asymptotic towards the point of surface level 42. This tailwater method is useful in checking and calibrating the point defined from the water front method.

As described herein, the water front method is needed to compute the depth of water 32 above ground 14 as it is passing and a constant depth of flow passes. Once a constant depth is achieved the volume above the surface back to point of inflow onto bay 12 can be determined. The input from monitoring the water level sensor 30 allows the change point 40 between the localized rate of filling principle to determine the measurement point of the mean ground level. Once the mean ground level 42 is detected as a point within the measurement range of the sensor 30, the depth of water 32 above ground level 14 can be determined by subtracting the surface level detection point from the sensor measurement.

This approach removes the need to know the absolute elevation of the water level sensor 30 relative to the mean ground level, as the water level sensor 30 now measures both the water depth 32 and the mean ground level 42 and provides a differential measurement which is not relative to the absolute position of the water level sensor 30. The depth of installation of the measuring cup 24 does not effect the measurement of depth above mean ground level, provided measuring cup 24 is below mean ground level.

When the water level sensor 30 is placed at a certain position (typically mid way along bay 12 between channels 20 and 22) and typically along the centreline of bay 12 it is possible to determine, once the maximum depth has been achieved, the following:

1. The volume applied to bay 12 up to the time water front 34 reaches the sensor position.
2. The volume above the surface level 42 up to the time water front 34 reaches the sensor position.
3. The infiltration up to the time water front 34 reaches the sensor position (the difference between 1. and 2. above).
4. The infiltration volume needed to complete the irrigation through to the end of bay 12.
5. The derivation of the cut off point 46 along the bay 12 at which the water front 34 arrives and the flow onto the bay 12 should stop.
6. The time for the water front 34 to reach the cut off point 46 and therefore close the gate or gates 18 and stop the flow onto bay 12.

Figure 4:
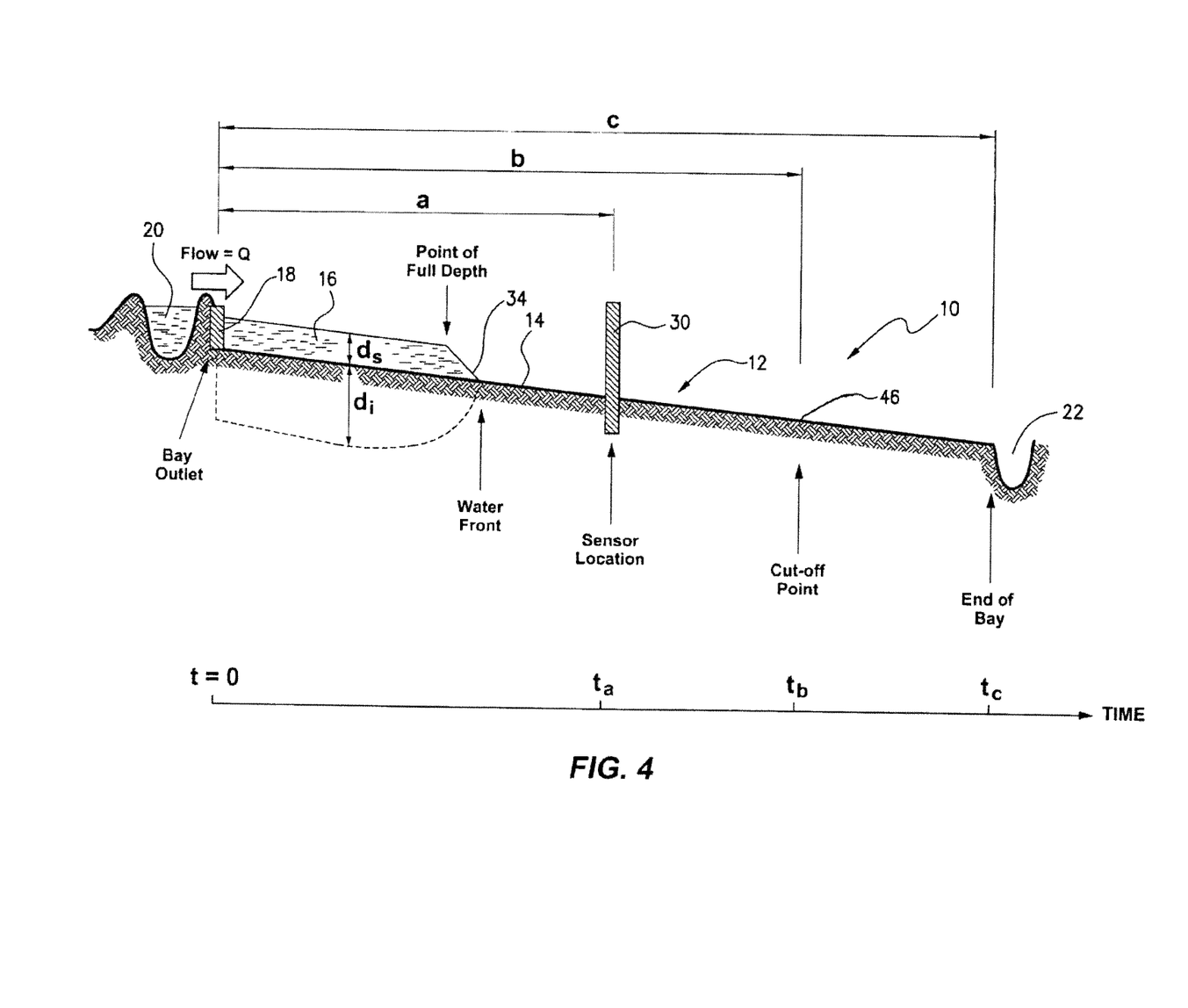
FIG. 4 is a larger view of FIG. 2 showing the calculations that can be made according to the method of the invention.

FIG. 4 shows the integers that are used in the determination of cut off point 46.

The integers are as follows:

a; distance from gate 18 to sensor 30
b; distance from gate 18 to cut off point 46
c; distance from gate 18 to open channel 22
$t_a$; time for water front 34 to reach sensor 30
$t_b$; time for water front 34 to reach cut off point 46
$t_c$; time for water front 34 to reach open channel 22
$d_s$; water depth above surface level 46
$d_i$; infiltration depth of water into the ground of bay 12
w; bay width (assume constant, although could vary)
Q; flow rate onto bay 12 (assume constant, although could vary)
$Q_w$; flow per unit width ($Q_w=Q/w$)
$V_w$; wedge volume (FIG. 2)—volume of water between water front 34 and the point at which full depth 48 is reached. (assume the wedge volume is negligible for the purposes of this example i.e. full depth 48 is at the point of water front 34)

When the water front 34 arrives at the sensor 30;

1. Total volume applied per unit width=$Q_w \times t_a$
2. Volume above surface per unit width=$a \times d_s$
3. Infiltration volume per unit width=$a \times d_i$ Therefore;

$$d_i = \left(\frac{Q_w \times t_a}{a}\right) - d_s$$

The remaining volume of water (per unit width) at time $t_a$ needed to accurately complete the irrigation;

$$= d_i \times (c-a)$$

The remaining volume of water (per unit width) at time $t_b$, needed to accurately complete the irrigation;

$$= d_i \times (c-b)$$

= the volume of water (per unit width) above the surface at $t_b$ $$= b \times d_s$$

Therefore;

$$b \times d_s = d_i \times (c-b)$$

$$b = \frac{(d_i \times c)}{(d_s + d_i)}$$

Assume the front moves at a constant velocity;

$$= \frac{a}{t_a} = \frac{b}{t_b}$$

$$t_b = \frac{b}{a} \times t_a$$

Or the time from when the water front reaches the sensor to when the flow onto the bay needs to be stopped;

$$= t_b - t_a$$

$$= \left(\frac{b}{a} \times t_a\right) - t_a$$

The method described above is for the use of one sensor 30 in a bay 12. The use of multiple sensors (not shown) can be used to give a more detailed measurement of the water level as well as the rate of travel of the water front.

FIGS. 5 to 10 illustrate a further aspect of the invention, namely an integrated soil moisture sensor 50. The ability to measure soil moisture enables determination of the optimal time to irrigate or apply water to the crop. The moisture sensor 50 can be used to allow measurement and calibration of the infiltration depth $d_i$; of water into the ground of bay 12 as previously discussed with reference to FIG. 4.

Traditional direct read soil moisture devices are vertically embedded into the soil. The techniques to measure soil moisture are capacitance or Time Domain Reflectometry (TDR). The problems with vertical embedded soil moisture sensors (capacitance or TDR) is the propensity for the water to run down the side (and the region of disturbed soil) of the vertical embedded sensor.

Figure 5:
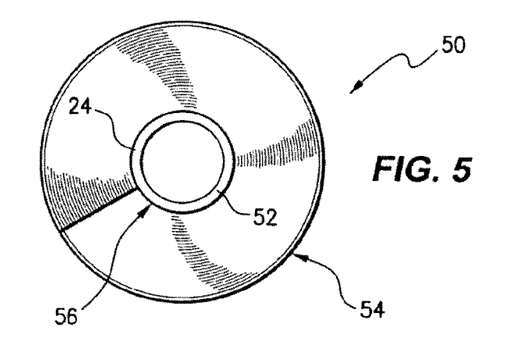
FIG. 5 is a plan view of a first embodiment of an auger which can be combined with the measuring cup shown in FIG. 1.
Figure 6:
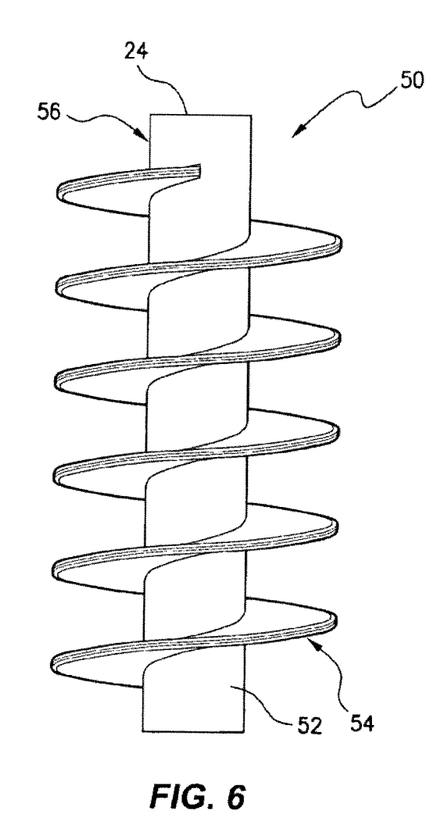
FIG. 6 is a side view of the auger shown in FIG. 5.
Figure 7:
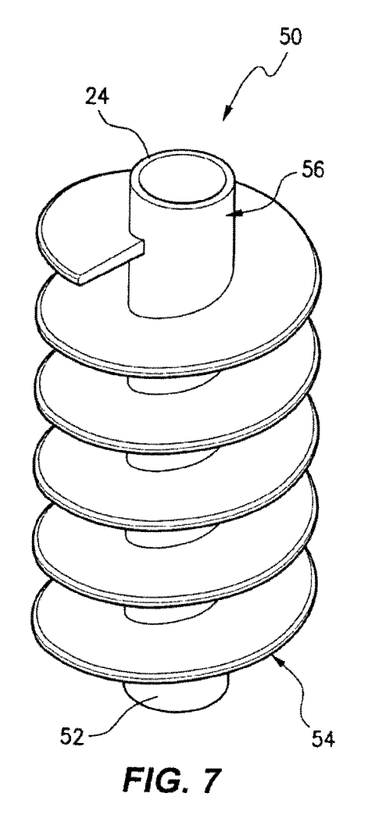
FIG. 7 is a top perspective view of the auger shown in FIG. 5.

FIGS. 5 to 7 show a central tube or column 52 with an external spiral 54 secured or integrated with central tube or column 52 to form an auger. In this embodiment the top section 56 of central tube or column 52 forms the measuring cup 24 with an internal base (not shown). Measuring cup 24 could also be separately attached to the central tube or column 52 as an alternative.

External spiral 54 can include at least one matching pair of:
1. capacitance plates facing each other; or
2. TDR probes attached thereto at the spiral edge.

Both alternatives could have multiple pairs or a combination of both pairs. The pairs could take advantage of alternate or offset spirals to mount each of the cooperating capacitance plates or TDR probes. The preferred option is to have two parallel plates with the pitch of the plates 180 degrees apart.

The advantage of the auger is that water is less prone to run down the inclined surface of the spiral 54 as compared to a vertical interface with the soil.

Figure 8:
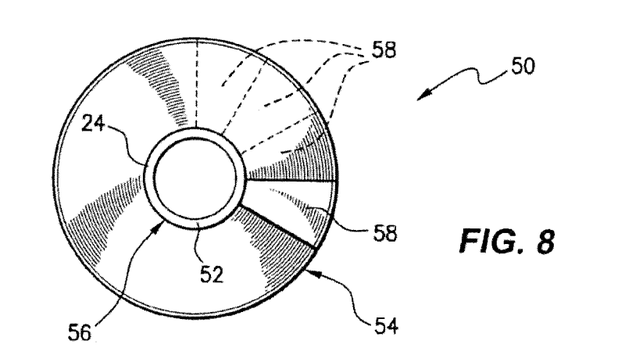
FIG. 8 is a second embodiment of an auger which can be combined with the measuring cup shown in FIG. 1.
Figures 9, 10:
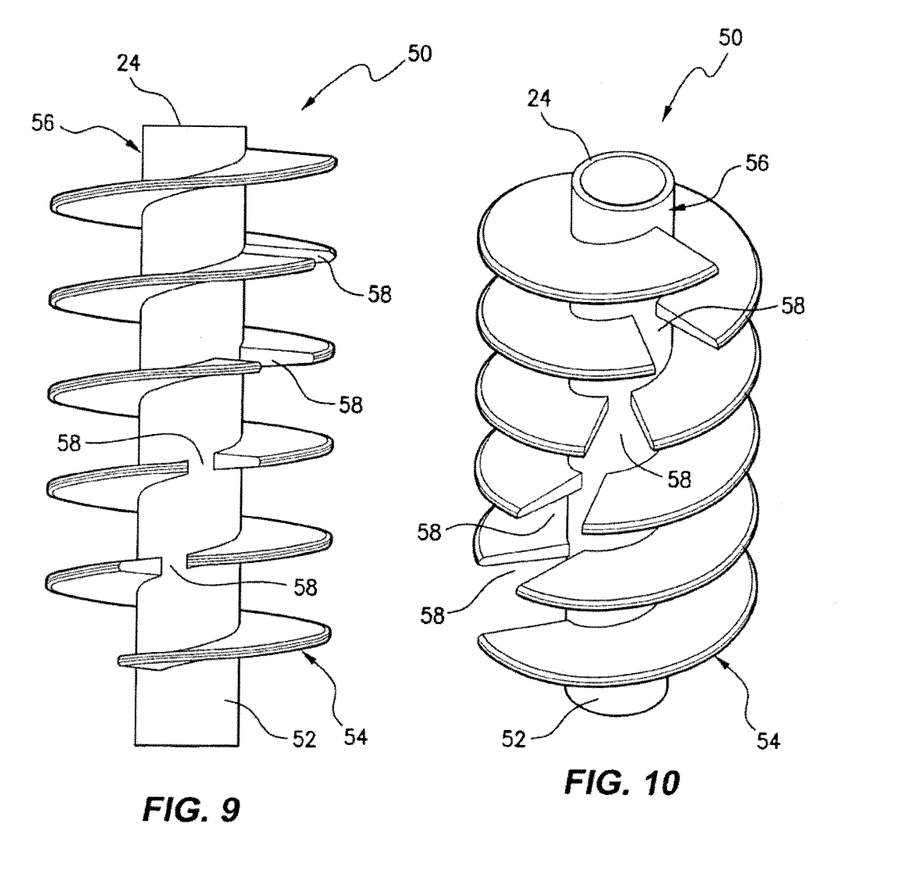
FIG. 9 is a side view of the auger shown in FIG. 8.
FIG. 10 is a top perspective view of the auger shown in FIG. 8.

In FIGS. 8 to 10 spiral 54 has discontinuities or breaks 58 such that at locations of the discontinuities 58 the soil will bind and prevent water running down the line of soil disturbance. Each segment or section of the discontinued spiral would then form a defined soil moisture device for a given depth—which is useful information for understanding the moisture content in soils. The discontinuities 58 typically traverse any desired degrees of arc.

The invention is not to be limited to the preferred embodiments described with reference to the drawings. Measuring cup 24 may be perforated to allow the measuring cup 24 to slowly empty when irrigation is completed. This will ensure that the measuring cup 24 will be empty for the next irrigation cycle.

Further advantages and improvements may very well be made to the present invention without deviating from its scope. Although the invention has been shown and described in what is conceived to be the most practical and preferred embodiment, it is recognized that departures may be made therefrom within the scope and spirit of the invention, which is not to be limited to the details disclosed herein but is to be accorded the full scope of the claims so as to embrace any and all equivalent devices and apparatus.

The claims defining the invention are as follows:

1. A method of determining a surface level of an area subject to flood, furrow or surface irrigation, said method including the steps of:
   providing at least one measuring cup positioned below the surface level but within the area;
   providing a water level sensor within or integrated with the at least one measuring cup;
   monitoring water levels provided by the water level sensor; and
   calculating the surface level by determining a change point at which increases in monitored water levels slow after a rapid increase of the monitored water levels.

2. The method of claim 1, wherein calculating the surface level comprises determining the change point at which increases in monitored water levels slow after the at least one measuring cup is filled with water, the at least one measuring cup having a taper directed downwardly towards a bottom of the at least one measuring cup.

3. The method of claim 1, further comprising determining a depth of water flowing over the at least one measuring cup, the determination based on a difference of monitored water levels of water flowing over the at least one measuring cup and the determined change point.

4. The method of claim 1, further comprising inserting the at least one measuring cup into a ground, a base of the at least one measuring cup including an auger to allow the at least one measuring cup to be inserted into the ground with reduced soil disturbance.

5. The method of claim 4, further comprising measuring soil moisture using the auger, the auger including means to measure the soil moisture.

6. The method of claim 5, wherein measuring the soil moisture using the auger comprises measuring soil moisture plates using capacitance plates of the auger to measure the soil moisture.

7. The method of claim 5, wherein measuring the soil moisture using the auger comprises using time domain reflectometry probes of the auger to measure the soil moisture.

8. The method of claim 5, wherein the measurement of the soil moisture is by either side of a screw of the auger having capacitance plates and/or edges of the screw of the auger having time domain reflectometry probes.

* * * * *